(12) United States Patent
DeVincenzo

(10) Patent No.: US 6,234,792 B1
(45) Date of Patent: *May 22, 2001

(54) ORTHODONTIC ATTACHMENT MEANS

(76) Inventor: John DeVincenzo, 1312 Garden St., San Luis Obispo, CA (US) 93401

( * ) Notice: Subject to any disclaimer, the term of this patent is extended or adjusted under 35 U.S.C. 154(b) by 0 days.

This patent is subject to a terminal disclaimer.

(21) Appl. No.: 09/429,653

(22) Filed: Oct. 29, 1999

(51) Int. Cl.[7] ............................................. A61C 3/00
(52) U.S. Cl. ............................................. 433/22; 433/19
(58) Field of Search ....................... 433/22, 18, 19, 433/7, 5, 6

(56) References Cited

U.S. PATENT DOCUMENTS

| | | | |
|---|---|---|---|
| 5,120,218 | * 6/1992 | Hanson | 433/19 |
| 5,378,147 | * 1/1995 | Mihailowitsch | 433/19 |
| 5,562,445 | 10/1996 | DeVincenzo et al. | 433/19 |
| 5,620,321 | * 4/1997 | Thornburg et al. | 433/19 |
| 5,738,514 | 4/1998 | DeVincenzo et al. | 433/19 |
| 5,829,975 | * 11/1998 | Gold | 433/19 |
| 5,853,291 | 12/1998 | DeVincenzo et al. | 433/176 |

* cited by examiner

*Primary Examiner*—Gene Mancene
*Assistant Examiner*—Melba Bumgarner
(74) *Attorney, Agent, or Firm*—Rodgers & Rodgers

(57) ABSTRACT

Orthodontic attachment means according to this invention comprises a ram which is an integral part of a plunger assembly, the ram being movable by means of a spring, a slotted cylinder rotatably attached to the ram, an aperture formed in the slotted cylinder, slot formed in the slotted cylinder and extending from the aperture, a base interconnected to a patient's teeth, a sphere integrally joined to the base by means of a neck, the sphere being dimensionally configured so as to be passable through the aperture, and the neck being slidable within the slot so as to interconnect the base and the slotted cylinder.

8 Claims, 2 Drawing Sheets

ORTHODONTIC ATTACHMENT MEANS

BACKGROUND OF THE INVENTION

This invention relates generally to orthodontic appliances wherein a force is applied between a patient's maxillary and mandibular dentitions. More specifically, U.S. Pat. No. 5,562,445 discloses plunger and molar assemblies wherein the molar assembly attaches to a molar tooth by means of an attachment wire. The plunger assembly slides within the molar assembly and attaches to the associated arch wire by means of a ram with a ring configuration disposed on the end thereof. By utilizing this arrangement, the practitioner is compelled to remove the entire arch wire in order to disassociate the plunger assembly from the patient's mouth. This is frequently required of the orthodondist due to either the breakage of an internal component or a desire to increase or decrease the amount of force the plunger assembly delivers. Of course, plunger assemblies of varying magnitudes of force are available.

In the eventuality that the plunger assembly malfunctions in a manner detected by the patient, normally in the neck area, or wherein the attachment wire breaks, it is impossible for the patient to remove the plunger assembly thereby necessitating an emergency office visit. If the patient happens to be out of town at the time of the breakage, another orthodontist would be required to remove the assembly.

SUMMARY OF THE INVENTION

Orthodontic attachment means comprising a base, a sphere spaced from the base by means of a neck, a cylinder attached at one end thereof to a plunger assembly, a slot formed in the cylinder remote from the plunger assembly with an aperture depending from one end thereof, and the neck being slidably receivable in the slot.

DESCRIPTION OF THE PREFERRED EMBODIMENT

Figure 1:
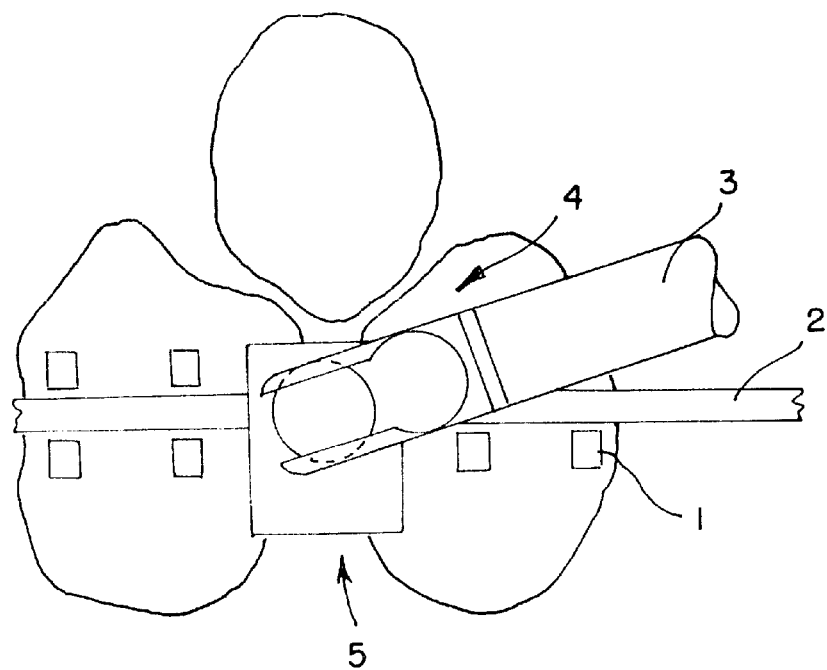
FIG. 1 is a front elevational view of the attachment means according to this invention.

In the drawings and with particular reference to FIG. 1, the numeral 1 designates conventional brackets which are adhered to a patient's teeth with arch wire 2 which is affixed to brackets 1 as is well known in the field of orthodontics. Numeral 3 designates the ram of the plunger assembly which is an integral part of the spring loaded plunger assembly as shown and described in U.S. Pat. No. 5,562,445. Affixed to ram 3, remote from the spring and cylinder elements, is slotted cylinder 4. Slotted cylinder 4 is interconnected with base 5 which, in turn, is affixed to arch wire 2.

Figure 4:
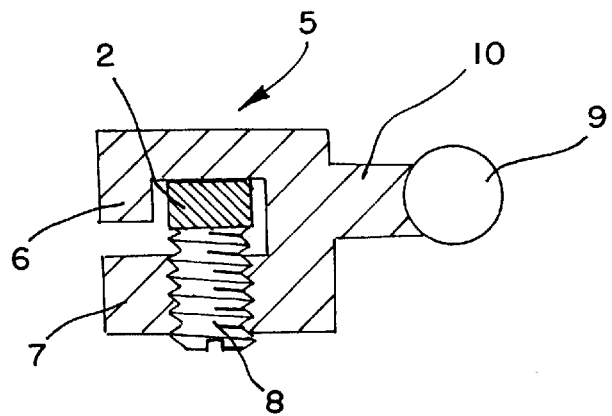
FIG. 4 is a side view of the attachment means with a portion thereof broken away.

The structure of base 5 is shown in more detail in FIG. 4 wherein two sides of base 5 cover arch wire 2 and finger 6 hooks behind arch wire 2. Base 5 includes member 7 having set screw 8 located to engage the fourth side of arch wire 2.

Thus, when set screw 8 is loosened, base 5 can be manipulated to place finger 6 behind arch wire 2. The top and front of arch wire 2 are then covered by base 5 and member 7 is positioned beneath arch wire 2. Set screw 8 can then be rotated until it abuts arch wire 2 to hold base 5 in place. Finally, sphere 9 is spaced outwardly from base 5 by means of neck 10.

Figure 5:
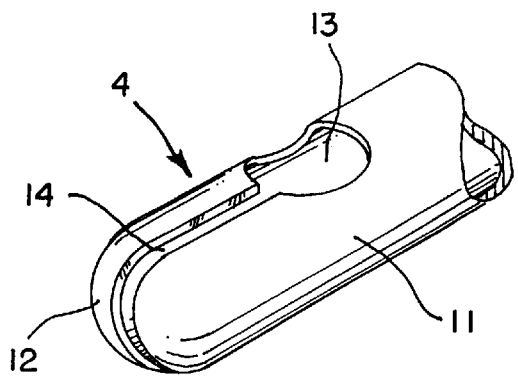
FIG. 5 is an enlarged perspective view of the slotted cylinder element of the attachment means.

Slotted cylinder 4 is shown in detail in FIG. 5 wherein elongated cylindrical body 11 is provided. One end of elongated body 11 is hemispherical as shown at 12. Disposed in cylindrical body 11 is generally circular aperture 13 and extending from aperture 13 around and past hemispherical end 12 is slot 14. Also, cylinder 4 is rotatably attached to ram 3 by suitable known coupling means 15.

Figure 2:
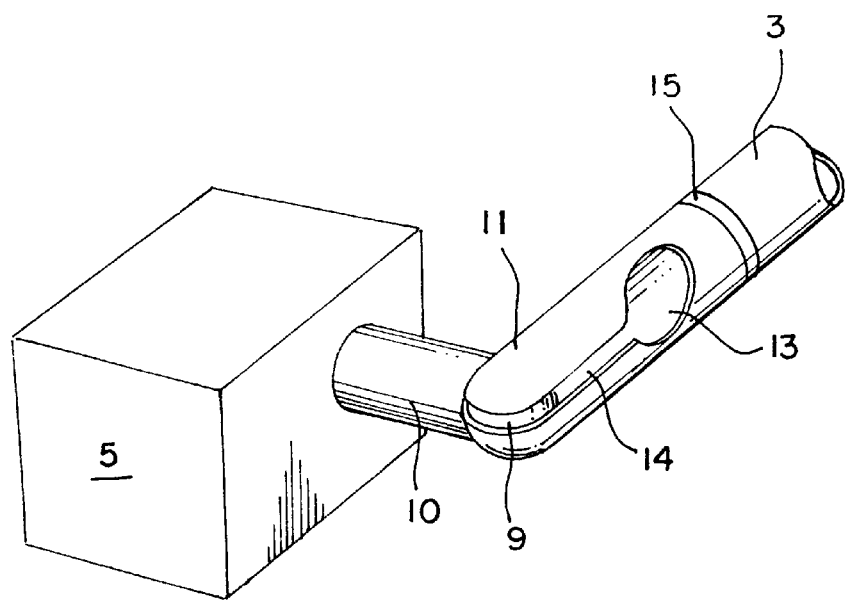
FIG. 2 is an enlarged perspective view of the attachment means shown in FIG. 1.
Figure 3:
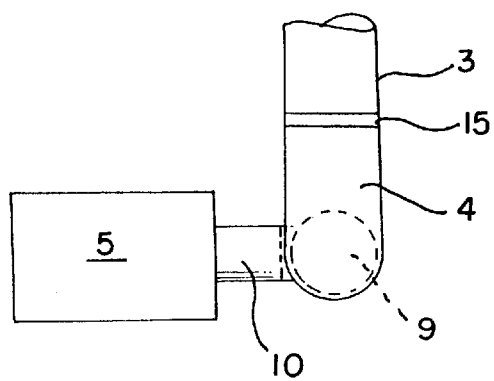
FIG. 3 is a top plan view of the attachment means.

In order to form the attachment means according to this invention, initially it is necessary to attach base 5 to arch wire 2 as previously described in connection with the structure shown in FIG. 4. Then it is necessary to manipulate sphere 9 through aperture 13 wherein neck 10 is then caused to slide through slot 14 into the position shown in FIGS. 1 and 2 whereby slotted cylinder 4 and base 5 are mechanically interconnected.

Therefore, by this invention, the orthodontist can easily remove the ram and associated spring and plunger assembly without going through the time consuming step of first removing the arch wire. Additionally, with the slotted cylinder configuration, even the patient can remove the ram and plunger assembly quickly and easily in the case of an emergency.

During the course of orthodontic treatment, frequently it is necessary to reduce or increase the amount of force delivered by ram 3 of the plunger assembly. By this invention, plunger assembly can be separated from arch wire 2 quickly and replaced with another assembly which delivers a different amount of force thereby saving a considerable amount of time. A related problem occurs when the internal spring breaks and then the quantity of force delivered thereby becomes inadequate. Again, by this invention, the broken spring can be replaced quickly and easily without removal of arch wire 2.

During mastication, the bent elbow of ram 3 in known devices, such as shown in U.S. Pat. No. 5,562,445, sometimes rotates toward the chewing surface of the teeth rather than staying in the vestibule of the cheek thereby causing severe damage to the ram, plunger assembly, teeth, arch wire and brackets which hold the arch wire to the teeth. Typically, when this occurs, the practitioner must undertake the time consuming step of using an extra wire or other means to stabilize the elbow portion of the ram so that it cannot rotate onto the chewing surface. By using the attachment means according to this invention, the elbow element of the ram is eliminated and the plunger assembly is prevented from rotating into the occlusion.

In addition, sphere 9 and associated neck 10 can be moved vertically and horizontally from the position shown in FIG. 1 which will change the force delivered by ram 3. A horizontal change alters the relationship of ram 3 assembly to the cheek vestibule on the one hand and the orthodontic band and bracket attachments on the other hand. Vertical changes move the ram assembly closer or farther away from the chewing surface.

What is claimed is:

1. Orthodontic attachment means comprising a base, a sphere integrally joined to said base by means of a neck, a cylinder, said cylinder comprising an aperture formed therein, a slot extending from said aperture, and said neck being slidable in said slot.

2. Orthodontic attachment means according to claim 1 wherein an arch wire is affixed to a patient's teeth and wherein said base is interconnected with said arch wire.

3. Orthodontic attachment means according to claim 2 wherein said base comprises a set screw for securing said base to said arch wire.

4. Orthodontic attachment means according to claim 1 wherein a portion of said cylinder is hemispherical and wherein said slot extends around said hemispherical portion.

5. Orthodontic attachment means according to claim 1 wherein said cylinder is attached to a ram and wherein said ram is detachably moveable with respect to said base.

6. Orthodontic attachment means according to claim 5 wherein said cylinder is rotatably attached to said ram.

7. An orthodontic attachment device comprising a cylinder, said cylinder comprising at least one end, said one end being hemispherical, an aperture formed in said cylinder, and a slot formed in said cylinder and extending from said aperture around said hemispherical end.

8. An orthodontic attachment device according to claim 7 wherein a ram is rotatably attached to said cylinder remote from said one end.

* * * * *